US005648499A

United States Patent [19]

Tanimoto et al.

[11] Patent Number: 5,648,499

[45] Date of Patent: *Jul. 15, 1997

[54] METHOD OF DECOMPOSING HALOGENATED AROMATIC COMPOUNDS

[75] Inventors: Fumio Tanimoto, Kyoto-hu; Tsuneo Yano, Saitama-ken, both of Japan

[73] Assignees: Mitsui & Co., Ltd., Kyoto-hu; Neos Co., Ltd, Tokyo; Research Institute for Production Development, Hyogo-ken, all of Japan

[ * ] Notice: The term of this patent shall not extend beyond the expiration date of Pat. No. 5,

[21] Appl. No.: 374,580

[22] PCT Filed: Jun. 23, 1994

[86] PCT No.: PCT/JP94/01002

§ 371 Date: Mar. 23, 1995

§ 102(e) Date: Mar. 23, 1995

[87] PCT Pub. No.: WO95/00207

PCT Pub. Date: Jan. 5, 1995

[30] Foreign Application Priority Data

Jun. 24, 1993 [JP] Japan .................................... 5-204389

[51] Int. Cl.$^6$ ........................ C07D 233/28; C07D 233/30

[52] U.S. Cl. ........................ 548/316.4; 570/204; 570/190; 568/672; 568/699; 568/868; 548/326.1

[58] Field of Search .................................... 570/190, 204; 568/868, 699, 672; 548/326.1, 316.4

[56] References Cited

U.S. PATENT DOCUMENTS

| | | | |
|---|---|---|---|
| 2,951,804 | 9/1960 | Juliard | 208/91 |
| 4,532,028 | 7/1985 | Peterson | 208/262 |
| 4,910,353 | 3/1990 | Siegman | 570/204 |

FOREIGN PATENT DOCUMENTS

| | | |
|---|---|---|
| 1181771 | 1/1985 | Canada . |
| 1206508 | 7/1983 | Italy . |

*Primary Examiner*—Jose G. Dees
*Assistant Examiner*—Rosalynd Williams
*Attorney, Agent, or Firm*—Burns, Doane, Swecker & Mathis LLP

[57] ABSTRACT

A safe and reliable method of decomposing halogenated aromatic compounds, wherein a heat-resistant alkaline polar solvent containing halogenated aromatic compounds is contacted with a alkali at a temperature ranging from about 100° C. to 300° C. in order to decompose the halogenated aromatic compounds. The used solvent is removed of solid contents of salts, alkalis and the like, whereby it can be recycled.

8 Claims, No Drawings

METHOD OF DECOMPOSING HALOGENATED AROMATIC COMPOUNDS

TECHNICAL FIELD

The present invention relates to a safe method of decomposing halogenated aromatic compounds such as polychlorinated biphenyl (hereinafter "PCB"), using chemical reaction of halogenated aromatic compounds in a polar solvent.

BACKGROUND ART

It is known that it is extremely difficult to treat PCB or other such halogenated aromatic compounds. This has led to considerable efforts directed toward the removal or decomposition of halogenated aromatic compounds. Methods for accomplishing this using a reaction process that takes place in the presence of an alkali include the alumina-alkali process disclosed by U.S. Pat. No. 2,951,804. U.S. Pat. No. 4,532,028 discloses a method of reacting alkali and a PCB content of up to 50,000 ppm in a mixture of alkyl or alkylene sulfoxide and polyol, thereby reducing the content to several ppm. Other examples include Canadian Pat. No. 1,181,771 which discloses a method employing melted sodium, and Italian Patent No. 22,215 which discloses a method using alkaline earth metal on which PEG is adsorbed.

Each method has its good points. However, with the prior art techniques it is not possible to further remove halogenated aromatic compounds from samples having a low concentration thereof, so that the halogenated aromatic compound content is further reduced to the extent that the inclusion thereof is substantially not recognizable; it is not yet possible to reduce the halogenated aromatic compound concentration to i ppm or below. Moreover, it is widely known that heating the solvent used in the prior art methods to a high temperature of 120° C. or over in the presence of an alkali or alkali metal has a chemically destablizing effect that promotes solvent decomposition and polymerization, degrading the basic function of the solvent.

SUMMARY

The inventor of the present invention investigated various ways of eliminating such drawbacks and discovered a highly effective method of decomposing halogenated aromatic compounds. In accordance with the method, a heat-resistant alkaline polar solvent that has a high boiling point and good high-temperature stability with respect to alkalis is selected, in which halogenated aromatic compounds are treated, using an alkali.

Thus, in the method of the present invention for decomposing halogenated aromatic compounds, the halogenated-aromatic compounds are contacted with an alkali at a temperature ranging from about 100° C. to about 300° C., and resultant solid materials contained in the heat-resistant alkaline polar solvent are removed therefrom.

Here, the halogenated aromatic compound is PCB and analogous compounds thereof.

In the method of the present invention, there were found to be slight differences in the halogenated aromatic compound decomposing effect of the various heat-resistant alkaline polar solvents. It was confirmed that 1, 3-dimethyl-2-imizazolidinone (herein after "DMI"), sulfolane, and also a mixture of 1, 3-dimethyl-2-imidazolidinone and sulfolane, are heat-resistant alkaline polar solvents that are effective under all of the conditions. Here, sulfolane when heated excessively generates odor, degrading operationability. Thus, it is preferable to use DMI, or a mixture of DMI and other solvent.

Depending on the purpose, ethylene glycol, diethylene glycol, triethylene glycol, polyethylene glycol, low alkyl-ethers of polyethylene glycol, trimethylene glycol, butylene glycol and low alkyl-ethers thereof are also effective. When the aim is to decompose halogenated aromatic compounds with high efficiency, it is preferable to use these solvents in an auxiliary role to make it easier to handle Industrially these heat-resistant alkaline polar solvents are used relatively extensively and have low toxicity and risk. What should be noted is their outstanding ability to dissolve halogenated aromatic compounds. While, in a conventional method, it has been recognized that a reaction rate of a halogenated aromatic compound and an alkali becomes extremely low if only an extraction process is used, the removal effect when the halogenated aromatic compounds are present in small quantities in the order of parts per million. According to repeated experiments using heat-resistant alkaline polar solvents of the present invention, it was found that the interaction between heat-resistant alkaline polar solvents and halogenated aromatic compounds was rapid and pronounced, and at high temperatures the effect was greater than expected, and that the halogenated aromatic compounds can be eliminated substantially.

While some effect is obtained even when a heat-resistant alkaline polar solvent and an alkali are contacted at a temperature of 100° C. or below, such a temperature will not produce a strong effect. On the other hand, although stable the heat-resistant alkaline polar solvent is an organic solvent and, as such., will gradually be degraded by a contact temperature of 300° C. or above. Therefore, preferably a contact temperature is used that is in the approximate range of from 100° C. to 300° C. for contact between the heat-resistant alkaline polar solvent and the alkali, and more preferably within the range of from 150° C. to 250° C.

Another factor involved in improving the efficiency with which halogenated aromatic compounds are decomposed is the method used for contacting the heat-resistant alkaline polar solvent with the alkali. The contact process can be effected using a reaction vessel and a stirrer, or a packed column and a circulation system, for example. The reaction efficiency can be improved by providing the packed column with an absorption layer in addition to the packing.

The final step in the method in accordance with the present invention involves the separation of salts such as sodium chloride, alkalis and the like from the processed heat-resistant alkaline polar solvent containing reaction products in a solid state as well as alkalis. After separation it is possible to recycle the heat-resistant alkaline polar solvent.

It is not easy to clarify how the structure of a halogenated aromatic compound thus removed has changed, as this will differ depending on the initial structure of the halogenated aromatic compound. Based on chemical commonsense it could be that chlorine substitutes for a hydroxyl group or bonds with alkyl-ether, but in either case it is important that chlorine be dissociated from the initial structure of the aromatic compound. In this invention, therefore, an alkali selected from the group consisting of sodium hydroxide, potassium hydroxide sodium alcholate, potassium alcoholate, and calcium hydroxide, may be used, preferably in a ratio of not less than 1.1 times the calculated halogen content of the heat-resistant alkaline polar solvent. According to the method of the present invention, halogenated aromatic compounds to be decomposed may be diluted, for example, with a solvent of hydrocarbon or other solvent. In either case, the halogenated aromatic compounds are treated in the heat-resistant polar solvent.

DETAILED DESCRIPTION OF THE PREFERRED EMBODIMENTS

Example 1

As listed in Table 1, a 100 g mixture of solvents (consisting of 65 g of DMI and 35 g of PEG200) containing about 1 weight percent of PCB was mixed with 2.6 g of potassium hydroxide (KOH, in Table 1) in a 300 ml flask, and the mixture was then stirred briskly while being maintained at a temperature of 200° C. for about 2 hours. After cooling the mixture to room temperature, the lower layer of solid was removed. After that, the PCB in the mixture was analyzed by GC-ECD, and it was confirmed that the PCB content had decreased to less than 0.5 mg/l. Since DMI has heat and alkaline stabilities, it can be recycled after solid materials are removed.

Example 2

As listed in Table 1, 190 g of DMI containing about 10 weight % of PCB was mixed with 13.5 g of sodium hydroxide (NaOH, in Table 1) in a 300 ml flask, and the mixture was then stirred briskly while being maintained at a temperature of 210° C. for about 3 hours. After cooling the mixture to room temperature, the lower layer of solid matter was removed and the PCB in the liquid was analyzed by GC-ECD, whereby it was confirmed that the PCB content had decreased to less than 0.5 mg/l. In this example and the following examples 3 to 10, the DMI from which the solid matter has been removed is recycled.

Example 3

As listed in Table 1, 190 g of DMI containing about 10 weight % of PCB was mixed with 1.4 g of sodium hydroxide in a 300 ml flask, and the mixture was then stirred briskly While being maintained at a temperature of 210° C. for about 3 hours. After cooling the mixture to room temperature, the lower layer of solid matter was removed and the PC8 in the liquid was analyzed by GC-ECD, whereby it was confirmed that the PCB content had decreased to less than 0.5 mg/l.

Example 4

As listed in Table 1, 190 g of DMI containing about 10 weight % of PCB was mixed with 16.7 g of sodium ethoxide (NaOEt, in Table 1) in a 300 ml flask, and the mixture was then stirred briskly while being maintained at a temperature of 160° C. for about 3 hours. After cooling the mixture to room temperature, the lower layer of solid matter was removed from the mixture and the PCB in the mixture was analyzed by GC-ECD, whereby it was confirmed that the PCB content had decreased to less than 0.5 mg/l.

Example 5

As listed in Table 1, 100g of a mixture of solvents (consisting of 63 g of DMI and 27 g of DEG) containing about 10 weight of PCB was mixed with 16.7 g of sodium ethoxide in a 300 ml flask, and the mixture was then stirred briskly while being maintained at a temperature of 190° C. for about 1.5 hours. After cooling the mixture to room temperature, the lower layer of solid was removed from the mixture. After that, the PCB in the mixture was analyzed by GC-ECD, whereby it has confirmed that the PCB content had decreased to less than 0.5 mg/l.

Example 6

As listed in Table 1, 100 g of a mixture of solvents (consisting of 63 g of DMI and 27 g of DEG) containing about 10 weight % of PCB was mixed with 13.4 g of sodium hydroxide in a 300 ml flask, and the mixture was then stirred briskly while being maintained at a temperature of 200° C. for about 3 hours. After cooling the mixture to room temperature, the lower layer of solid was removed from the mixture. After that, the PCB in the mixture was analyzed by GC-ECD, whereby it has confirmed that the PCB content had decreased to less than 0.5 mg/l.

Example 7

As listed in Table 1, 100 g of DMI containing about 1 weight % of PCB was mixed with 1.91 g of sodium hydroxide in a 300 ml flask, and the mixture was then stirred briskly while being maintained at a temperature of 200° C. for about 2 hours. After cooling the mixture to room temperature, the lower layer of solid matter was removed from the mixture and the chlorinated biphenyl in the mixture was analyzed for every contents thereof by the method of SIM using GC-MS. The results are: the content of monochlorinated biphenyl was less than 0.6 mg/l, and those of dichlorinated biphenyl, trichlorinated biphenyl, tetrachlorinated biphenyl, pentachlorinated biphenyl, octachlorinated biphenyl, nonachlorinated biphenyl, decachlorinated biphenyl were less than 0.1 mg/l, respectively. Accordingly, it was confirmed that the PCB content had decreased to less than 0.6 mg/l.

Example 8

As listed in Table 1, 100 g of DMI containing about 1 weight % of PCB was mixed with 1.91 g of sodium hydroxide in a 300 ml flask, and the mixture was then stirred briskly while being maintained at a temperature of 200° C. for about 3 hours. After cooling the mixture to room temperature, the lower layer of solid matter was removed from the mixture and the chlorinated biphenyl in the mixture was analyzed for every contents thereof in the same manner as that of Example 7, whereby it was confirmed that each of the contents of chlorinated biphenyls was less than 0.1 mg/l and that the PCB content had decreased to less than 0.1 mg/l.

Example 9

As listed in Table 1, 100 g of DMI containing about 1 weight % of PCB was mixed with 3.34 g of sodium ethoxide in a 300 ml flask, and the mixture was then stirred briskly while being maintained at a temperature of 200° C. for about 2 hours. After cooling the mixture to room temperature, the lower layer of solid matter was removed from the mixture and the chlorinated biphenyl in the mixture was analyzed for every contents thereof in the same manner as that of Example 7, whereby it was confirmed that each of the contents of chlorinated biphenyls was less than 0. 1 mg/l and that the PCB content had decreased to less than 0.1 mg/l.

Example 10

As listed in Table 1, 100 g of DMI containing about 1 weight % of PCB was mixed with 1.3 g of calcium oxide or calcium hydroxide (CaO, in Table 1) in a 300 ml flask, and the mixture was then stirred briskly while being maintained at a temperature of 200° C. for about 3 hours. After cooling the mixture to room temperature, the lower layer of solid matter was removed from the mixture and the chlorinated biphenyl in the mixture was analyzed for every contents thereof in the same manner as that of Example 7, whereby it was confirmed that each of the contents of chlorinated biphenyls was less than 0.1 mg/l and that the PCB content had decreased to less than 0.1 mg/l.

Comparative Example 1

As listed in Table 1, 100 g of mixture of solvents (consisting of 35 g of DMI and 65 g of PEG200) containing about 1 weight percent of PCB was mixed with 1.91 g of sodium hydroxide in a flask, and the mixture was then stirred briskly while being maintained at a temperature of 200° C. for about 2 hours. After cooling the mixture to room temperature, the lower layer of solid matter was removed from the mixture. After that, the PCB in the mixture was analyzed by GC-ECD, and it was found that the PCB content was 2.6 mg/l.

Comparative Example 2

As listed in Table 1, 100 g of sulfolane containing about 1 weight % of PCB was mixed with 3.34 g of sodium ethoxide in a flask, and the mixture was then stirred briskly while being maintained at a temperature of 160° C. for about 2 hours. After cooling the mixture to room temperature, the lower layer of solid matter was removed from the mixture. After that, the PCB in the mixture was analyzed by GC-ECD, and it was found that the PCB content was 340 mg/l.

Comparative Example 3

As listed in Table 1, 100 g of mixture of solvents (consisting of 50 g of sulfolane and 50 g of DEG) containing about 1 weight % of PCB was mixed with 1.91 g of sodium hydroxide in a flask, and the mixture was then stirred briskly while being maintained at a temperature of 205° C. for about 2 hours. After cooling the mixture to room temperature, the lower layer of solid matter was removed from the mixture. After that, the PCB in the mixture was analyzed by GC-ECD, and it was found that the PCB content was 64 mg/l.

Thus, in each of the inventive examples PCB was removed with good efficiency.

TABLE 1

| Conditions | Sample solvent (g) | Sample PCB (g) | Sample Cl (mol.) | Alkali (g) | Processing temperature (°C.) | Processing time (Hr) | Remaining PCB content (mg/l) |
|---|---|---|---|---|---|---|---|
| Inventive examples | | | | | | | |
| 1 | DMI 65 PEG 35 | 1.036 | 0.0159 | KOH 2.6 | 200 | 2 | below 0.5 |
| 2 | DMI 90 | 10.00 | 0.1539 | NaOH 13.5 | 210 | 3 | below 0.5 |
| 3 | DMI 90 | 10.02 | 0.1531 | NaOH 1.4 | 210 | 3 | below 0.5 |
| 4 | DMI 90 | 9.810 | 0.1509 | NaOEt 16.7 | 160 | 3 | below 0.5 |
| 5 | DMI 63 DEG 27 | 10.01 | 0.1541 | NaOEt 16.7 | 190 | 1.5 | below 0.5 |
| 6 | DMI 63 DEG 27 | 10.01 | 0.1541 | NaOH 13.7 | 200 | 3 | below 0.5 |
| 7 | DMI 100 | 1.036 | 0.0159 | NaOH 1.91 | 200 | 2 | below 0.6 |
| 8 | DMI 100 | 1.036 | 0.0159 | NaOH 1.91 | 200 | 3 | below 0.1 |
| 9 | DMI 100 | 1.036 | 0.0159 | NaOEt 3.34 | 200 | 2 | below 0.1 |
| 10 | DMI 100 | 1.036 | 0.0159 | CaO/KOH 1.3/2.0 | 200 | 3 | below 0.1 |
| Comparative examples | | | | | | | |
| 1 | DMI 35 PEG 65 | 1.029 | 0.0158 | NaOH 1.91 | 200 | 2 | 2.6 |
| 2 | Sulfolane 100 | 0.998 | 0.0154 | NaOEt 3.34 | 160 | 2 | 340 |
| 3 | Sulfolane 50 DEG 50 | 1.020 | 0.0157 | NaOH 1.91 | 205 | 2 | 64 |

Industrial Applicability

As described in the foregoing, in accordance with the present invention, PGB and other such halogenated aromatic compounds which, even in small quantities, pose environmental problems and are directly hazardous to the human body, can be removed to the extent that the PCB or other such compound is rendered substantially harmless. In addition, the heat-resistant alkaline polar solvents which were used to treat halogenated aromatic compounds can be recycled.

We claim:

1. A method of decomposing halogenated aromatic compounds, comprising: contacting a heat-resistant alkaline polar solvent which contains 15 weight % or less of halogenated aromatic compounds with an alkali at a temperature ranging from about 100° C. to about 300° C., and then separating resultant solid contents from said heat-resistant alkaline polar solvent, wherein the halogenated aromatic compounds are polychlorinated biphenyls and said heat-resistant alkaline polar solvent is 1,3-dimethyl-2-imidazolidinone.

2. A method of decomposing halogenated aromatic compounds, comprising: contacting a heat-resistant alkaline polar solvent which contains 15 weight % or less of halogenated aromatic compounds with an alkali at a temperature ranging from about 100° C. to about 300° C., and then separating resultant solid contents from said heat-resistant alkaline polar solvent, wherein the halogenated aromatic compounds are polychlorinated biphenyls and said heat-resistant alkaline polar solvent is a mixture of 1,3-dimethyl-2-imidazolidinone and at least one solvent selected from the group consisting of ethylene glycol, diethylene glycol, triethylene glycol, polyethylene glycol, low alkyl-ethers of polyethylene glycol, trimethylene glycol, butylene glycol and low alkyl-ethers thereof.

3. The method according to claim 1, in which said heat-resistant polar solvent and said alkali are contacted at a temperature ranging from about 150° C. to about 250° C.

4. The method according to claim 2, in which said heat-resistant polar solvent and said alkali are contacted at a temperature ranging from about 150° C. to about 250° C.

5. The method according to claim 1, in which said alkali is at least one of alkalis selected from a group consisting of sodium hydroxide, potassium hydroxide, sodium alcholate, potassium alcholate, and calcium hydroxide.

6. The method according to claim 1, in which said alkali is a mixture of alkalis selected from a group consisting of sodium hydroxide, potassium hydroxide, sodium alcholate, potassium alcholate, and calcium hydroxide.

7. The method according to claim 2, in which said alkali is at least one of alkalis selected from a group consisting of sodium hydroxide, potassium hydroxide, sodium alcholate, potassium alcholate, and calcium hydroxide.

8. The method according to claim 2, in which said alkali is a mixture of alkalis selected from a group consisting of sodium hydroxide, potassium hydroxide, sodium alcholate, potassium alcholate, and calcium hydroxide.

* * * * *

UNITED STATES PATENT AND TRADEMARK OFFICE

CERTIFICATE OF CORRECTION

PATENT NO. : 5,648,499

DATED : July 15, 1997

INVENTOR(S) : Fumio TANIMOTO et al

It is certified that error appears in the above-indentified patent and that said Letters Patent is hereby corrected as shown below:

On the title page:

In item [*], delete "5," and insert -- 5,476,987 --.

Signed and Sealed this

Seventh Day of October, 1997

Attest:

BRUCE LEHMAN

*Attesting Officer* *Commissioner of Patents and Trademarks*